United States Patent
Onimus et al.

(10) Patent No.: US 6,972,337 B1
(45) Date of Patent: Dec. 6, 2005

(54) EPOXIDATION CATALYST

(75) Inventors: Wilson H. Onimus, Holmes, PA (US); Bernard Cooker, Malvern, PA (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 0 days.

(21) Appl. No.: 10/918,605

(22) Filed: Aug. 12, 2004

(51) Int. Cl.$^7$ ............................................ C07D 301/06
(52) U.S. Cl. ...................................... 549/533; 549/531
(58) Field of Search ................................ 549/531, 533

(56) References Cited

U.S. PATENT DOCUMENTS

| | | | |
|---|---|---|---|
| 3,351,635 A | 11/1967 | Kollar | 260/348.5 |
| 4,136,063 A * | 1/1979 | Kimura et al. | 502/314 |
| 4,367,342 A | 1/1983 | Wulff et al. | 549/529 |
| 4,410,501 A | 10/1983 | Taramasso et al. | 423/326 |
| 4,833,260 A | 5/1989 | Neri et al. | 549/531 |
| 4,937,216 A | 6/1990 | Clerici et al. | 502/62 |
| 5,859,265 A | 1/1999 | Muller et al. | 549/531 |
| 6,063,942 A * | 5/2000 | Grey | 549/523 |
| 6,310,224 B1 * | 10/2001 | Grey | 549/523 |
| 6,417,378 B1 * | 7/2002 | Hancu | 549/533 |

FOREIGN PATENT DOCUMENTS

| | | |
|---|---|---|
| BE | 1001038 A7 | 6/1989 |
| JP | 4-352771 | 12/1992 |
| WO | WO 98/00413 | 1/1998 |

* cited by examiner

Primary Examiner—Cecilia J. Tsang
Assistant Examiner—Raymond Covington
(74) Attorney, Agent, or Firm—Kevin M. Carroll

(57) ABSTRACT

Titanium or vanadium zeolites are heated at a temperature greater than 400° C., then contacted with water prior to use in olefin epoxidation with hydrogen peroxide.

20 Claims, No Drawings

EPOXIDATION CATALYST

FIELD OF THE INVENTION

This invention relates to an epoxidation process to produce epoxides from olefins and hydrogen peroxide using a titanium or vanadium zeolite catalyst that has been pre-treated by heating at a temperature greater than 400° C. and then contacting with water.

BACKGROUND OF THE INVENTION

Many different methods for the preparation of epoxides have been developed. Generally, epoxides are formed by the reaction of an olefin with an oxidizing agent in the presence of a catalyst. The production of propylene oxide from propylene and an organic hydroperoxide oxidizing agent, such as ethyl benzene hydroperoxide or tert-butyl hydroperoxide, is commercially practiced technology. This process is performed in the presence of a solubilized molybdenum catalyst, see U.S. Pat. No. 3,351,635, or a heterogeneous titania on silica catalyst, see U.S. Pat. No. 4,367,342. Another commercially practiced technology is the direct epoxidation of ethylene to ethylene oxide by reaction with oxygen over a silver catalyst. Unfortunately, the silver catalyst has not proved useful in commercial epoxidation of higher olefins.

Besides oxygen and alkyl hydroperoxides, another oxidizing agent useful for the preparation of epoxides is hydrogen peroxide. U.S. Pat. Nos. 4,833,260, 4,410,501, and 4,937,216, for example, disclose the epoxidation of olefins with hydrogen peroxide in the presence of a titanium silicate catalyst.

Much current research is conducted in the direct epoxidation of olefins with oxygen and hydrogen. In this process, it is believed that oxygen and hydrogen react in situ to form an oxidizing agent. Many different catalysts have been proposed for use in the direct epoxidation of higher olefins. Typically, the catalyst comprises a noble metal that is supported on a titanosilicate. For example, JP 4-352771 discloses the formation of propylene oxide from propylene, oxygen, and hydrogen using a catalyst containing a Group VIII metal such as palladium on a crystalline titanosilicate. The Group VIII metal is believed to promote the reaction of oxygen and hydrogen to form an in situ oxidizing agent. U.S. Pat. No. 5,859,265 discloses a catalyst in which a platinum metal, selected from Ru, Rh, Pd, Os, Ir and Pt, is supported on a titanium or vanadium silicalite. Other direct epoxidation catalyst examples include gold supported on titanosilicates, see for example PCT Intl. Appl. WO 98/00413.

As with any chemical process, it is desirable to attain still further improvements in the epoxidation methods and catalysts. We have discovered an effective, convenient process to form an epoxidation catalyst and its use in the epoxidation of olefins.

SUMMARY OF THE INVENTION

The invention is a process for producing epoxides from olefins and hydrogen peroxide using a pre-treated titanium or vanadium zeolite catalyst, wherein the zeolite catalyst is pre-treated by heating at a temperature greater than 400° C. and then contacting with water. The process of the invention results in higher selectivity to the desired epoxide.

DETAILED DESCRIPTION OF THE INVENTION

The epoxidation process of the invention utilizes a titanium or vanadium zeolite. Titanium or vanadium zeolites comprise the class of zeolitic substances wherein titanium or vanadium atoms are substituted for a portion of the silicon atoms in the lattice framework of a molecular sieve. Such substances, and their production, are well known in the art. See for example, U.S. Pat. Nos. 4,410,501 and 4,833,260.

Titanium or vanadium zeolites comprise the class of zeolitic substances wherein titanium or vanadium atoms are substituted for a portion of the silicon atoms in the lattice framework of a molecular sieve. Such substances, and their production, are well known in the art. See for example, U.S. Pat. Nos. 4,410,501 and 4,833,260. Particularly preferred titanium zeolites include the class of molecular sieves commonly referred to as titanium silicalites, particularly "TS-1" (having an MFI topology analogous to that of the ZSM-5 aluminosilicate zeolites), "TS-2" (having an MEL topology analogous to that of the ZSM-11 aluminosilicate zeolites), and "TS-3" (as described in Belgian Pat. No. 1,001,038). Titanium-containing molecular sieves having framework structures isomorphous to zeolite beta, mordenite, ZSM-48, ZSM-12, and MCM-41 are also suitable for use. The titanium zeolites preferably contain no elements other than titanium, silicon, and oxygen in the lattice framework, although minor amounts of boron, iron, aluminum, sodium, potassium, copper and the like may be present.

The synthesis of titanium or vanadium zeolites is well known in the art. Titanium or vanadium zeolite synthesis typically comprises reacting a titanium or vanadium compound, a silicon source, and a templating agent at a temperature and for a time sufficient to form a titanium or vanadium zeolite. Suitable titanium compounds useful in titanium zeolite synthesis include, but are not limited to, titanium alkoxides and titanium halides. Preferred titanium alkoxides are titanium tetraisopropoxide, titanium tetraethoxide and titanium tetrabutoxide. Suitable silicon sources include, but are not limited to, colloidal silica, fumed silica and silicon alkoxides. Preferred silicon alkoxides are tetraethylorthosilicate, tetramethylorthosilicate, and the like. Tetraethylorthosilicate is especially preferred. The templating agent is typically a tetraalkylammonium hydroxide, tetraalkylammonium halide, tetraalkylammonium nitrate, tetraalkylammonium acetate, and the like. Tetraalkylammonium hydroxides and tetraalkylammonium halides, such as tetrapropylammonium hydroxide and tetrapropylammonium halide, are preferred. Tetrapropylammonium hydroxide is especially preferred.

Synthesis of titanium or vanadium zeolites is carried out by a hydrothermal crystallization of a reaction mixture prepared by combining the titanium or vanadium compound, silicon source, and templating agent in the presence of water. Other solvents such as alcohols may also be present. Alcohols such as isopropyl, ethyl and methyl alcohol are preferred, and isopropyl alcohol is especially preferred.

Generally, the hydrothermal process used to prepare titanium or vanadium zeolites involves forming a reaction mixture wherein the molar ratios of additives (as defined in terms of moles of templating agent, moles of $SiO_2$ and moles of $TiO_2$ or $VO_{2.5}$) comprise the following molar ratios: $TiO_2(VO_{2.5}):SiO_2=0.5–5:100$; and templating agent: $SiO_2=10–50:100$. The water:$SiO_2$ molar ratio is typically from about 1000–5000:100 and the solvent:$SiO_2$ molar ratio may be in the range of 0–500:100.

The reaction mixture is prepared by mixing the desired sources of titanium or vanadium, silicon and templating agent to give the reaction mixture. It is also typically necessary that the mixture have a pH of about 9 to about 13. The basicity of the mixture is controlled by the amount of templating agent (if it is in the hydroxide form) which is added and the use of other basic compounds. If another basic compound is used, the basic compound is preferably an organic base that is free of alkali metals, alkaline earth metals, and the like. The addition of other basic compounds may be needed if the templating agent is added as a salt, e.g., halide or nitrate. Examples of these basic compounds include ammonium hydroxide, quaternary ammonium hydroxides and amines. Specific examples include tetraethylammonium hydroxide, tetrabutylammonium hydroxide, n-butylamine, and tripropylamine.

After the reaction mixture is formed, it is reacted at a temperature and a time sufficient to form a molecular sieve. Typically, the reaction mixture is heated at a temperature of about 100° C. to about 250° C. for a period of about 0.5 hours to about 96 hours in a sealed vessel under autogenous pressure. Preferably, the reaction mixture is heated at a temperature range from about 125° C. to about 200° C., most preferably from about 150° C. to about 180° C. After the desired reaction time, the titanium or vanadium zeolite is recovered. Suitable zeolite recovery methods include filtration and washing (typically with deionized water), rotary evaporation, centrifugation, and the like. The titanium or vanadium zeolite may be dried at a temperature greater than about 20° C., preferably from about 50° C. to about 200° C.

As synthesized, the titanium or vanadium zeolites of this invention will contain some of the templating agent or the additional basic compounds in the pores. The titanium or vanadium zeolite is pre-treated by first heating at temperatures greater than about 400° C., typically from about 450° C. to about 1000° C., and preferably from about 475° C. to about 600° C. This heating step is necessary to decompose the templating agent contained in the pores. If the assynthesized titanium or vanadium zeolite is produced in the form of a powder, it may be spray dried, pelletized or extruded prior to the heating step. If spray dried, pelletized or extruded, the titanium or vanadium zeolite may additionally comprise a binder or the like and may be molded, spray dried, shaped or extruded into any desired form prior to or after the heating step.

Preferably, the heated titanium or vanadium zeolite may undergo a second thermal treatment. If a second thermal treatment is conducted, the titanium or vanadium zeolite is typically heated at temperatures greater than about 250° C., typically from about 300° C. to about 1200° C., preferably from about 550° C. to about 950° C., and most preferably from about 700° C. to about 900° C. The second thermal treatment is typically performed following cooling the titanium or vanadium zeolite to less than 100° C., preferably to less than 35° C.

The high temperature heating step or steps may be conducted in inert atmosphere which is substantially free of oxygen, such as nitrogen, argon, neon, helium or the like or mixture thereof. By "substantially free of oxygen", it is meant that the inert atmosphere contains less than 10,000 ppm mole oxygen, preferably less than 2000 ppm. Also, the heating may be conducted in an oxygen-containing atmosphere, such as air or a mixture of oxygen and an inert gas. Alternatively, the catalyst may also be heated in the presence of an inert gas such as nitrogen prior to heating in an oxygen-containing atmosphere. The heating process may be conducted such that the gas stream (inert, oxygen-containing, or both) is passed over the titanium or vanadium zeolite. Alternatively, the heating may be performed in a static manner. The zeolite could also be agitated or stirred while being contacted with the gas stream.

Following the heating step or steps, the titanium or vanadium zeolite is then contacted with water. The water that is used in the contacting step is preferably significantly free of impurities. By "significantly free", it is meant that the water contains less than 10,000 ppm impurities (preferably less than 2000 ppm) and has a neutral pH in the range of 6 to 8. Any conventional washing procedure is suitable. The temperature of water contact is not crucial to the invention, however lower temperatures may require a longer contact period. Preferably, the titanium or vanadium zeolite is contacted with water at a temperature greater than 50° C. More preferred wash temperatures are greater than 60° C., most preferably from 65° C. to 95° C. Pressures of from 0 to 1000 psig are generally useful for purposes of this invention. Preferably, the pressure is sufficient to maintain the water substantially as a liquid phase when elevated temperatures are used.

Contacting preferentially also encompasses separating the water from the used contacted zeolite. For instance, after contacting with water, the titanium or vanadium zeolite may be collected by filtration, centrifugation, decantation, or other such mechanical means prior to use in the epoxidation reaction of the invention. After contacting with water and collecting the zeolite by filtration, centrifugation, decantation, or other such mechanical means, the titanium or vanadium zeolite may also be dried. The drying may be performed under vacuum, with heating, or a combination.

The contacting procedure may be carried out in a continuous or a batch-type process. In a fixed bed embodiment of the invention, it is preferred to pass the contacting water through the titanium or vanadium zeolite as a flowing stream such that water effluent is continually carried away from the fixed bed. The contacting water could be recirculated. Liquid hourly space velocities in the range of from 0.1 to 24 are generally satisfactory. When the contacting is performed as a batch-type process, the titanium or vanadium zeolite may be contacted with water by agitating the water and removing the supernatant solution. The contacting time is preferably in the range of from about 1 hour to 30 days.

After contacting the zeolite with water, the titanium or vanadium zeolite may be used in the epoxidation process as a powder or as a large particle size solid. If the pre-treated titanium or vanadium zeolite is still in the form of a powder, it may preferably be spray dried, pelletized or extruded prior to epoxidation. If spray dried, pelletized or extruded, the titanium or vanadium zeolite may additionally comprise a binder or the like and may be molded, spray dried, shaped or extruded into any desired form.

The epoxidation process of the invention comprises contacting an olefin and hydrogen peroxide in the presence of the pre-treated titanium or vanadium zeolite catalyst. Suitable olefins include any olefin having at least one carbon—carbon double bond, and generally from 2 to 60 carbon atoms. Preferably the olefin is an acyclic alkene of from 2 to 30 carbon atoms; the process of the invention is particularly suitable for epoxidizing $C_2$–$C_6$ olefins. More than one double bond may be present, as in a diene or triene for example. The olefin may be a hydrocarbon (i.e., contain only carbon and hydrogen atoms) or may contain functional groups such as halide, carboxyl, hydroxyl, ether, carbonyl, cyano, or nitro groups, or the like. The process of the invention is especially useful for converting propylene to propylene oxide.

The hydrogen peroxide may be generated prior to use in the epoxidation reaction. Hydrogen peroxide may be derived from any suitable source, including oxidation of secondary alcohols such as isopropanol, the anthraquinone process, and from direct reaction of hydrogen and oxygen. The concentration of the aqueous hydrogen peroxide reactant added into the epoxidation reaction is not critical. Typical hydrogen peroxide concentrations range from 0.1 to 90 weight percent hydrogen peroxide in water, preferably 1 to 5 weight percent.

The amount of hydrogen peroxide to the amount of olefin is not critical, but most suitably the molar ratio of hydrogen peroxide:olefin is from 100:1 to 1:100, and more preferably in the range of 10:1 to 1:10. One equivalent of hydrogen peroxide is theoretically required to oxidize one equivalent of a mono-unsaturated olefin substrate, but it may be desirable to employ an excess of one reactant to optimize selectivity to the epoxide.

The hydrogen peroxide may also be generated in situ by the reaction of hydrogen and oxygen in the presence of a noble metal catalyst. Although any sources of oxygen and hydrogen are suitable, molecular oxygen and molecular hydrogen are preferred.

While any noble metal catalyst can be utilized (i.e., gold, silver, platinum, palladium, iridium, ruthenium, osmium metal catalysts), either alone or in combination, palladium, platinum and gold metal catalysts are particularly desirable. Suitable noble metal catalysts include high surface area noble metals, noble metal alloys, and supported noble metal catalysts. Examples of suitable noble metal catalysts include high surface area palladium and palladium alloys. However, particularly preferred noble metal catalysts are supported noble metal catalysts comprising a noble metal and a support.

For supported noble metal catalysts, the support is preferably a porous material. Supports are well-known in the art. There are no particular restrictions on the type of support that are used. For instance, the support can be inorganic oxides, inorganic chlorides, carbon, and organic polymer resins. Preferred inorganic oxides include oxides of Group 2, 3, 4, 5, 6, 13, or 14 elements. Particularly preferred inorganic oxide supports include silica, alumina, titania, zirconia, niobium oxides, tantalum oxides, molybdenum oxides, tungsten oxides, amorphous titania-silica, amorphous zirconia-silica, amorphous niobia-silica, and the like. Preferred organic polymer resins include polystyrene, styrene-divinylbenzene copolymers, crosslinked polyethyleneimines, and polybenzimidizole. Suitable supports also include organic polymer resins grafted onto inorganic oxide supports, such as polyethylenimine-silica. Preferred supports also include carbon. Particularly preferred supports include carbon, silica, silica-aluminas, titania, zirconia, and niobia.

Preferably, the support has a surface area in the range of about 10 to about 700 $m^2/g$, more preferably from about 50 to about 500 $m^2/g$, and most preferably from about 100 to about 400 $m^2/g$. Preferably, the pore volume of the support is in the range of about 0.1 to about 4.0 mL/g, more preferably from about 0.5 to about 3.5 mL/g, and most preferably from about 0.8 to about 3.0 mL/g. Preferably, the average particle size of the support is in the range of about 0.1 to about 500 $\mu$m, more preferably from about 1 to about 200 $\mu$m, and most preferably from about 10 to about 100 $\mu$m. The average pore diameter is typically in the range of about 10 to about 1000 Å, preferably about 20 to about 500 Å, and most preferably about 50 to about 350 Å. In one preferred embodiment of the invention, the supported noble metal catalyst comprises a noble metal supported on the pre-treated titanium or vanadium zeolite.

The supported noble metal catalyst contains a noble metal. While any of the noble metals can be utilized (i.e., gold, silver, platinum, palladium, iridium, ruthenium, osmium), either alone or in combination, palladium, platinum and gold are particularly desirable, and palladium is especially preferred. Typically, the amount of noble metal present in the supported catalyst will be in the range of from 0.001 to 20 weight percent, preferably 0.005 to 10 weight percent, and particularly 0.01 to 5 weight percent. The manner in which the noble metal is incorporated into the catalyst is not considered to be particularly critical. For example, the noble metal may be supported on the zeolite by impregnation, adsorption, precipitation, or the like. Alternatively, the noble metal can be incorporated into the zeolite by ion-exchange with, for example, tetraammine palladium dichloride.

There are no particular restrictions regarding the choice of noble metal compound or complex used as the source of the noble metal in the supported catalyst. For example, suitable compounds include the nitrates, sulfates, halides (e.g., chlorides, bromides), carboxylates (e.g. acetate), and amine complexes of noble metals. The noble metal may be in an oxidation state anywhere from 0 to +4 or any combination of such oxidation states. To achieve the desired oxidation state or combination of oxidation states, the noble metal compound may be calcined, reduced, or a combination thereof. Satisfactory catalytic performance can, however, be attained without any pre-reduction. To achieve the active state of noble metal, the supported noble metal catalyst may undergo pretreatment such as thermal treatment in nitrogen, vacuum, hydrogen, or air.

In one preferred embodiment of the invention, the epoxidation of olefin, hydrogen and oxygen is carried out in the presence of a noble metal-containing titanium or vanadium zeolite which comprises a noble metal and the pre-treated titanium or vanadium zeolite.

Depending on the olefin to be reacted, the epoxidation according to the invention can be carried out in the liquid phase, the gas phase, or in the supercritical phase. When a liquid reaction medium is used, the catalyst is preferably in the form of a suspension or fixed-bed. The process may be performed using a continuous flow, semi-batch or batch mode of operation.

If epoxidation is carried out in the liquid (or supercritical) phase, it is advantageous to work at a pressure of 1–100 bars and in the presence of one or more solvents. Suitable solvents include, but are not limited to, alcohols, water, supercritical $CO_2$, or mixtures thereof. Suitable alcohols include $C_1$–$C_4$ alcohols such as methanol, ethanol, isopropanol, and tert-butanol, or mixtures thereof. Fluorinated alcohols can be used. It is preferable to use mixtures of the cited alcohols with water.

If epoxidation is carried out in the liquid (or supercritical) phase, it is advantageous to use a buffer. The buffer will typically be added to the solvent to form a buffer solution. The buffer solution is employed in the reaction to inhibit the formation of glycols or glycol ethers during epoxidation. Buffers are well known in the art.

Buffers useful in this invention include any suitable salts of oxyacids, the nature and proportions of which in the mixture, are such that the pH of their solutions may range from 3 to 10, preferably from 4 to 9 and more preferably from 5 to 8. Suitable salts of oxyacids contain an anion and cation. The anion portion of the salt may include anions such as phosphate, carbonate, bicarbonate, carboxylates (e.g., acetate, phthalate, and the like), citrate, borate, hydroxide, silicate, aluminosilicate, or the like. The cation portion of the salt may include cations such as ammonium, alkylammoniums (e.g., tetraalkylammoniums, pyridiniums, and the like), alkali metals, alkaline earth metals, or the like. Cation examples include $NH_4$, $NBu_4$, $NMe_4$, Li, Na, K, Cs, Mg, and Ca cations. More preferred buffers include alkali metal phosphate and ammonium phosphate buffers. Buffers may preferably contain a combination of more than one suitable salt. Typically, the concentration of buffer in the solvent is from about 0.0001 M to about 1 M, preferably from about 0.001 M to about 0.3 M. The buffer useful in this invention may also include the addition of ammonia gas to the reaction system. The process of the invention may be carried out in a batch, continuous, or semi-continuous manner using any appropriate type of reaction vessel or apparatus such as a fixed-bed, transport bed, fluidized bed, stirred slurry, or CSTR reactor. The catalyst is preferably in the form of a suspension or fixed-bed. Known methods for conducting metal-catalyzed epoxidations of olefins using an oxidizing agent will generally also be suitable for use in this process. Thus, the reactants may be combined all at once or sequentially.

Epoxidation according to the invention is carried out at a temperature effective to achieve the desired olefin epoxidation, preferably at temperatures in the range of 0–150° C., more preferably, 20–120° C. Reaction or residence times of from about 1 minute to 48 hours, more preferably 1 minute to 8 hours will typically be appropriate. It is advantageous to work at a pressure of 1 to 100 atmospheres, although the reaction can also be performed at atmospheric pressure.

The following examples merely illustrate the invention. Those skilled in the art will recognize many variations that are within the spirit of the invention and scope of the claims.

EXAMPLE 1

Preparation of TS-1 Catalyst

TS-1 may be prepared according to any standard procedure. A typical procedure follows:

A dry 1-liter stainless steel autoclave, with a nitrogen purge, agitator, thermocouple, addition ports and valves, and an over-pressure relief disc, is set in an ice bath to cool it to 0° C. The autoclave is purged under nitrogen feed and tetraethyl orthosilicate (TEOS, 364 g) is charged to the vessel and the agitator is run at 1000 rpm. Tetraethyl orthotitanate (TEOT, 11.2 g) is then added over 30 to 60 minutes, with vigorous mixing, while maintaining the ice bath cooling. A 12.5 wt. % aqueous solution of tetrapropyl ammonium hydroxide (TPAOH, prepared by adding 200 g of 40 wt. % aqueous TPAOH and 440 g of deionized water) is then added to the vessel over 4 hours, with continued cooling. After TPAOH addition, the ice bath is removed and stirring is continued until the mixture reaches room temperature. The resulting gel is stirred at 225 rpm and heated to 180° C., held at 180° C. for 24 hours, and then cooled. The TS-1 product crystals are filtered, washed three times with deionized water (200 g), and then dried under vacuum at 55° C. for 2 hours.

Comparative Catalyst 1A: The TS-1 produced above is oven calcined in air by heating from 20 to 110° C. at 10° C./min and holding at 110° C. for 2 hours, then heating to 550° C. at 2° C./min and holding at 550° C. for 4 hours to produce Comparative Catalyst 1A.

Comparative Catalyst 1B: A portion of Catalyst 1A is further oven calcined in air by heating from 20 to 110° C. at 10° C./min and holding at 110° C. for 2 hours, then heating to 350° C. at 2° C./min and holding at 350° C. for 4 hours to produce Comparative Catalyst 1B.

Comparative Catalyst 1C: A portion of Catalyst 1A is further oven calcined in air by heating from 20 to 110° C. at 10° C./min and holding at 110° C. for 2 hours, then heating to 550° C. at 2° C./min and holding at 550° C. for 4 hours to produce Comparative Catalyst 1C.

Comparative Catalyst 1D: A portion of Catalyst 1A is further oven calcined in air by heating from 20 to 110° C. at 10° C./min and holding at 110° C. for 2 hours, then heating to 800° C. at 2° C./min and holding at 800° C. for 4 hours to produce Comparative Catalyst 1 D.

Comparative Catalyst 1 E: A portion of Catalyst 1A is further oven calcined in air by heating from 20 to 110° C. at 10° C./min and holding at 110° C. for 2 hours, then heating to 950° C. at 2° C./min and holding at 950° C. for 4 hours to produce Comparative Catalyst 1 E.

Comparative Catalyst 1 F: A portion of Catalyst 1A is further oven calcined in air by heating from 20 to 110° C. at 10° C./min and holding at 110° C. for 2 hours, then heating to 1100° C. at 2° C./min and holding at 1100° C. for 4 hours to produce Comparative Catalyst 1 F.

EXAMPLE 2

Water Treatment of TS-1 Catalyst

Comparative Catalysts 1A, 1B, 1C, 1D, 1E, AND 1F are separately and identically treated by making a 10 wt. % slurry of each catalyst in deionized water in a Teflon flask, with nitrogen purging, followed by rapid heating to 65° C., and maintaining at 65° C. for 7 days. The solids are then filtered and dried under vacuum at 55° C. for 16 hours. The water treatment of Catalyst 1A gave Catalyst 2A; the water treatment of Catalyst 1 B yielded Catalyst 2B; the water treatment of Catalyst 1C gave Catalyst 2C; the water treatment of Catalyst 1D gave Catalyst 2D; the water treatment of Catalyst 1 E gave Catalyst 2E; and the water treatment of Catalyst 1 F gave Catalyst 2F.

EXAMPLE 3

Epoxidation of Propylene

Comparative Catalysts 1A–1F and Catalysts 2A–2F are used in batch epoxidation of propylene with hydrogen peroxide according to the following procedure:

In a 100 mL stainless steel reactor, catalyst (0.15 g) is added to a 5 wt. % hydrogen peroxide solution prepared by mixing aqueous hydrogen peroxide (6.67 g of 30 wt. % $H_2O_2$) with methanol (33.33 g). Liquid propylene (20 g) is added to the reaction mixture and the batch reaction is run for 30 minutes at 50° C. under agitation via a stir bar at 1000 rpm and 225 psig of autogenous pressure. The product liquid and gas phases are analyzed by gas chromatography (GC) and by titration, yielding the data shown in Table 1. Propylene oxide and equivalents ("POE"), which include propylene oxide ("PO"), propylene glycol, and glycol ethers, are produced during the reaction.

The experimental results show that PO/POE selectivity improves in all cases following the water washing step, particularly at 800° C., showing a decrease in unwanted ring opening products.

TABLE 1

COMPARISON OF CATALYST ACTIVITY

| Catalyst | H₂O₂ Conversion (%) | PO produced (mmol) | POE produced (mmol) | PO/POE Selectivity (%)¹ |
|---|---|---|---|---|
| 1A* | 85.65 | 41.8 | 47.42 | 88.15 |
| 1B* | 84.4 | 42.54 | 48.08 | 88.48 |
| 1C* | 85.18 | 43.03 | 48.18 | 89.31 |
| 1D* | 76.35 | 38.41 | 43.38 | 88.54 |
| 1E* | 68.83 | 33.77 | 38.01 | 88.85 |
| 1F* | 43.85 | 21.42 | 24.06 | 89.03 |
| 2A | 84.63 | 43.42 | 46.98 | 92.44 |
| 2B | 80.85 | 41.25 | 45.76 | 90.15 |
| 2C | 80.75 | 39.39 | 43.67 | 90.2 |
| 2D | 73.5 | 40.41 | 41.55 | 97.25 |
| 2E | 67.21 | 36.07 | 37.86 | 95.28 |
| 2F | 50.07 | 24.43 | 25.5 | 95.81 |

*Comparative Example
¹PO/POE Selectivity = moles PO/(moles PO + moles glycols + moles glycol ethers) * 100.

We claim:

1. A process for producing an epoxide which comprises reacting an olefin with hydrogen peroxide in the presence of a titanium or vanadium zeolite, wherein the titanium or vanadium zeolite is pre-treated by heating at a temperature greater than 400° C. and then contacting with water.

2. The process of claim 1 wherein the titanium or vanadium zeolite is a titanium silicalite.

3. The process of claim 1 wherein the titanium or vanadium zeolite is TS-1.

4. The process of claim 1 wherein the olefin is a $C_2$–$C_6$ olefin.

5. The process of claim 1 wherein the titanium or vanadium zeolite is contacted with water at a temperature greater than 50° C.

6. The process of claim 1 wherein reaction of olefin and hydrogen peroxide is performed in a solvent selected from the group consisting of water, $C_1$–$C_4$ alcohols, supercritical $CO_2$, and mixtures thereof.

7. The process of claim 1 wherein the titanium or vanadium zeolite is additionally heated at a temperature greater than 250° C. following the heating at a temperature greater than 400° C. and prior to the contacting with water.

8. The process of claim 7 wherein the additional heating is conducted at a temperature of 700° C. to 900° C.

9. The process of claim 1 wherein the hydrogen peroxide is formed by the in situ reaction of hydrogen and oxygen in the presence of a noble metal catalyst.

10. The process of claim 9 wherein the noble metal catalyst comprises a noble metal and a support.

11. The process of claim 10 wherein the noble metal is selected from the group consisting of palladium, platinum, and gold.

12. The process of claim 10 wherein the support is selected from the group consisting of carbon, titania, zirconia, niobium oxides, silica, alumina, silica-alumina, tantalum oxides, molybdenum oxides, tungsten oxides, titania-silica, zirconia-silica, niobia-silica, and mixtures thereof.

13. A process for producing an epoxide comprising reacting an olefin, hydrogen and oxygen in the presence of a noble metal-containing titanium or vanadium zeolite comprising a noble metal and a titanium or vanadium zeolite, wherein the titanium or vanadium zeolite is pre-treated by heating at a temperature greater than 400° C. and then contacting with water.

14. The process of claim 13 wherein the titanium or vanadium zeolite is a titanium silicalite.

15. The process of claim 13 wherein the titanium or vanadium zeolite is TS-1.

16. The process of claim 13 wherein the olefin is a $C_2$–$C_6$ olefin.

17. The process of claim 13 wherein the olefin is propylene.

18. The process of claim 13 wherein the titanium or vanadium zeolite is contacted with water at a temperature greater than 50° C.

19. The process of claim 13 wherein reaction of olefin, hydrogen and oxygen is performed in a solvent selected from the group consisting of water, $C_1$–$C_4$ alcohols, supercritical $CO_2$, and mixtures thereof.

20. The process of claim 13 wherein the titanium or vanadium zeolite is additionally heated at a temperature greater than 250° C. following the heating at a temperature greater than 400° C. and prior to the contacting with water.

* * * * *